United States Patent [19]
Türker et al.

[11] Patent Number: 5,911,250
[45] Date of Patent: Jun. 15, 1999

[54] FILLING ADAPTER FOR A METERING DEVICE

[75] Inventors: Ahmet Türker; Rolf Brückner; Siegfried Baumgarten, all of Lübeck; Heye Harms, Stockelsdorf, all of Germany

[73] Assignee: Drägerwerk Aktiengesellschaft, Lübeck, Germany

[21] Appl. No.: 08/791,639

[22] Filed: Jan. 31, 1997

[30] Foreign Application Priority Data

Aug. 21, 1996 [DE] Germany ............... 296 14 491

[51] Int. Cl.⁶ .................................................. B65B 3/00
[52] U.S. Cl. .................. 141/94; 141/18; 141/95; 141/198; 137/392
[58] Field of Search ..................... 141/18, 21, 94, 141/95, 198; 137/392

[56] References Cited

U.S. PATENT DOCUMENTS

| | | | |
|---|---|---|---|
| 4,326,851 | 4/1982 | Bello et al. ............... | 141/198 |
| 4,469,149 | 9/1984 | Walkey et al. ............ | 141/94 |
| 4,506,709 | 3/1985 | Dennhardt ................ | 141/95 |
| 4,852,621 | 8/1989 | Bear ........................... | 141/83 |
| 4,913,196 | 4/1990 | Williams et al. .......... | 141/1 |
| 5,144,991 | 9/1992 | Wallroth et al. .......... | 141/18 |
| 5,279,338 | 1/1994 | Goossens .................. | 141/95 |
| 5,417,258 | 5/1995 | Privas ........................ | 141/18 |
| 5,465,766 | 11/1995 | Siegele et al. ............ | 141/198 |
| 5,474,112 | 12/1995 | Carola ....................... | 141/18 |
| 5,493,840 | 2/1996 | Cane .......................... | 141/94 |
| 5,507,326 | 4/1996 | Cadman et al. .......... | 141/198 |
| 5,609,191 | 3/1997 | Topping et al. .......... | 141/198 |

FOREIGN PATENT DOCUMENTS 41 06 756 A1  9/1992  Germany.

Primary Examiner—J. Casimer Jacyna
Attorney, Agent, or Firm—McGlew and Tuttle, P.C.

[57] ABSTRACT

A filling adapter is provided for connecting a reservoir filled with a liquid with a metering device, which filling adapter has a liquid-specific connection piece for the reservoir. A code device is provided, detectable by the metering device, at least for the liquid contained in the reservoir. The code device is provided on the filling adapter in the connection area between the filling adapter and the metering device.

18 Claims, 4 Drawing Sheets

FILLING ADAPTER FOR A METERING DEVICE

FIELD OF THE INVENTION

The present invention pertains to a filling adapter for connecting a reservoir filled with a liquid with a said metering device, which filling adapter has a liquid-specific connection piece for the reservoir.

BACKGROUND OF THE INVENTION

A filling adapter, which has a connection piece at one end for connection to a reservoir filled with an anesthetic and is provided at the other end with a coupling piece, which can be pushed into an insertion opening of an anesthetic-metering device, has been known from DE 41 06 756 A1. The filling adapter is designed in a manner specific of the anesthetic, i.e., it can be connected to a certain reservoir only, and the coupling piece can also be pushed only into the insertion opening of the corresponding anesthetic-metering device. It shall thus be ensured that an anesthetic-metering device is filled with the correct anesthetic.

The drawback of the prior-art device is that a corresponding number of anesthetic-metering devices are needed for metering different anesthetics.

SUMMARY AND OBJECTS OF THE PRESENT INVENTION

The primary object of the present invention is to improve a device of the above-described type such that a plurality of reservoirs can be connected to a single metering device.

This object is accomplished by a code for the liquid contained in the reservoir, which code can be recognized by the metering device, being provided on the filling adapter in the connection area between the filling adapter and the metering device.

According to the invention, a filling adapter is provided for connecting a reservoir filled with a liquid with a metering device, which filling adapter has a liquid-specific connection piece for the reservoir. A code means is provided, detectable by the metering device, at least for the liquid contained in the reservoir. The code means is provided on the filling adapter in the connection area between the filling adapter and the metering device.

The advantage of the present invention is essentially that due to the code, the metering device receives information on the liquid that is to be fed to a user. It is possible due to the code to set a metering pump located in the metering device to the physical data of the liquid.

It is especially advantageous to arrange a detection means for the code on the metering device, which detection means is connected to a measuring and monitoring device within the metering device and in which a comparison of the code detected with a code pattern present in a stored set is performed. In the case of agreement between the code and the code pattern, the measuring and monitoring device sends a corresponding control signal to a metering pump located in the metering device.

It is especially advantageous to design the code as an opto-electronically detectable, coded strip.

It is advantageous for the code to be designed as a permanent memory, whose memory contents are read by a detection means located in the connection area.

A filling channel or venting channel located on the bottle adapter advantageously has a pressure-limiting valve. It shall be achieved with the pressure-limiting valve that a vacuum possibly present in the reservoir can be eliminated toward the environment.

A suction system extending from the connection piece into the reservoir is advantageously designed as a filling level indicator. It is especially advantageous for the capacitive transducer to be designed such that a suction tube is accommodated within an outer tube in an insulated manner. Due to the annular space filling with liquid between the suction tube and the outer tube, a change in capacitance is generated, depending on the filling level of the liquid within the reservoir, and this change in capacitance can be detected by measurement.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
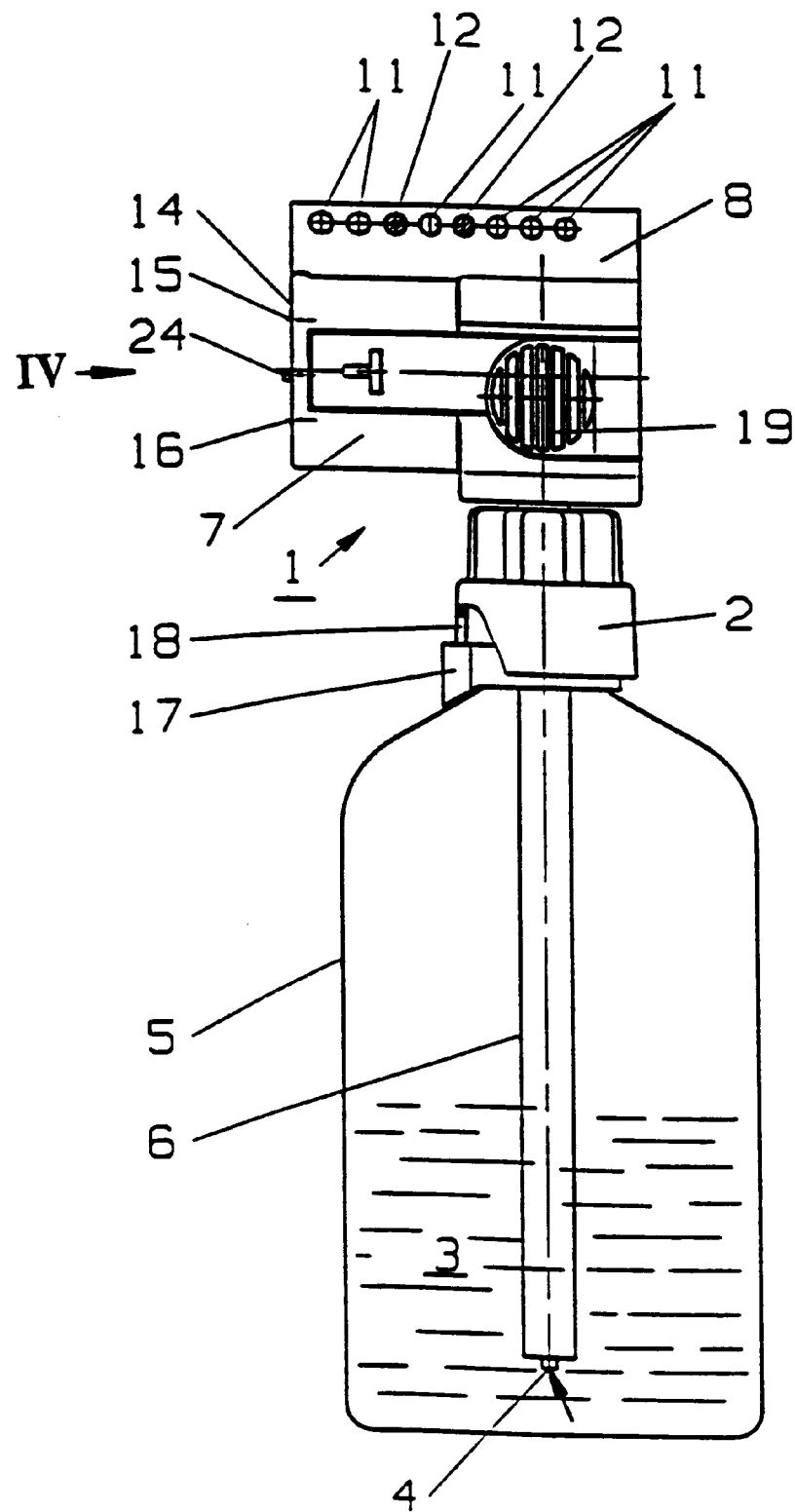
FIG. 1 is a side view of a filling adapter and an insertion opening to a metering device shown as a longitudinal section.

Referring to the drawings in particular, FIG. 1 shows a filling adapter 1, which is connected at one end to a reservoir 5 filled with a liquid anesthetic 3 via a coded connection piece 2. The liquid anesthetic 3 is delivered from the reservoir 5 via a suction tube 4. An outer tube 6 is arranged coaxially with the suction tube, electrically insulated from same, and the suction tube 4 and the outer tube 6 together form a capacitive transducer in order to detect the filling level of the liquid anesthetic 3 within the reservoir 5. The other end of the filling adapter 1 is designed as a coupling piece 7 with an opto-electronically evaluable coded strip 8, which can be pushed into an insertion opening 9 of a metering device 10. The coded strip 8 has individual perforations 11 and sections 12 that are transparent to light, which provide information on the liquid 3 present in the reservoir 5 in a binary coded form and can be evaluated by individual light barriers 13 located opposite the perforations 11 and the sections 12 that are transparent to light in the metering device 10, acting as a detection means. The connection area between the filling adapter 1 and the metering device 10 is the overlapping area of the coupling piece 7 with coded strips 8 within the insertion opening 9. A filling channel 15 and a venting channel 16, which are in connection with the suction tube 4 and with the interior space of the reservoir 5, which is filled with liquid 3, open on the front side 14 of the coupling piece 7. A filling channel 15 is also arranged within the insertion opening 9, and the filling channel is designed as a first control pin 151 projecting in the manner of a bar. A star-like coding piece 17, which belongs to the liquid anesthetic 3 and engages corresponding recesses 18 on the connection piece 2, is arranged on the bottleneck of the reservoir 5. Such a coding for liquid anesthetic reservoirs is described in the basic safety standard of German DIN (Deutsche Institut für Normung) 13252. It is achieved with the coding piece 17 that only reservoirs 5 containing a defined liquid anesthetic 3 can be connected to the filling adapter 1. The code predetermined by the coding piece 17 for a defined liquid anesthetic 3 is transferred as a binary code to the coded strip 8. Besides the type of the liquid anesthetic 3, the capacity of the reservoir 5 can also be transmitted to the metering device 10 by using different filling adapters 1 with different threads within the connection piece 2 for different reservoir volumes, and the type of the thread is also included in the coding of the strip 8.

The bottle adapter 1 is designed as a recessed grip 19 in its part offset by 90° between the coupling piece 7 and the connection piece 2. The coupling piece 7 can thus be pushed into the insertion opening 9 especially easily.

The metering device 10 schematically shown in FIG. 1 comprises, besides the insertion opening 9 with the light barriers 13, a metering and monitoring device 20 and a metering pump 21. The measuring and monitoring device 20 processes the code detected by the light barriers 13 and compares same with code patterns which are stored in a memory, not shown in FIG. 1. A defined code pattern is associated with each liquid anesthetic 3. Liquid-specific control signals, which are transmitted to the metering pump 21 via a control line 22, are obtained from the code pattern. The metering pump 21 is connected to the filling channel 15 via a delivery line 23 and draws in the liquid anesthetic 3 through the suction tube 4 if the coupling piece 7 is inserted into the insertion opening. The pressure is equalized within the reservoir 5 via the venting channel 16 as a consequence of the volume of liquid removed. The filling level of the liquid anesthetic 3 is transmitted to the measuring and monitoring unit 20 by a capacitive transducer formed by the suction tube 4 and the outer tube 6 and via contact points 24 on the front side of the coupling piece 7 and within the insertion opening 9, as well as a signal line 25 connected to the contact points 24. If the filling in the reservoir 5 drops below a minimum amount, a warning signal is generated by the measuring and monitoring device 20.

Figure 2:
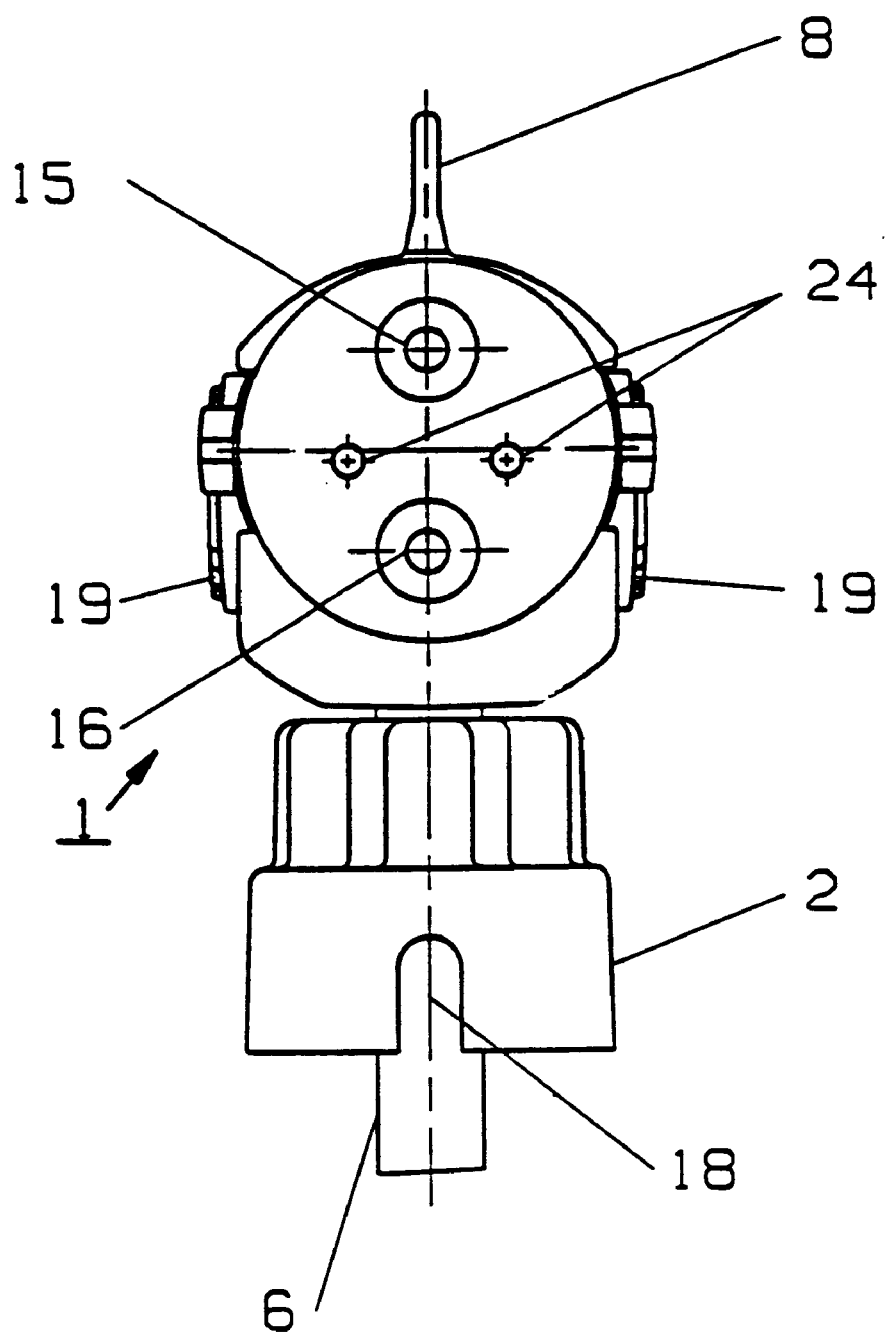
FIG. 2 is a filling adapter in the viewing direction A according to FIG. 1.
Figure 3:
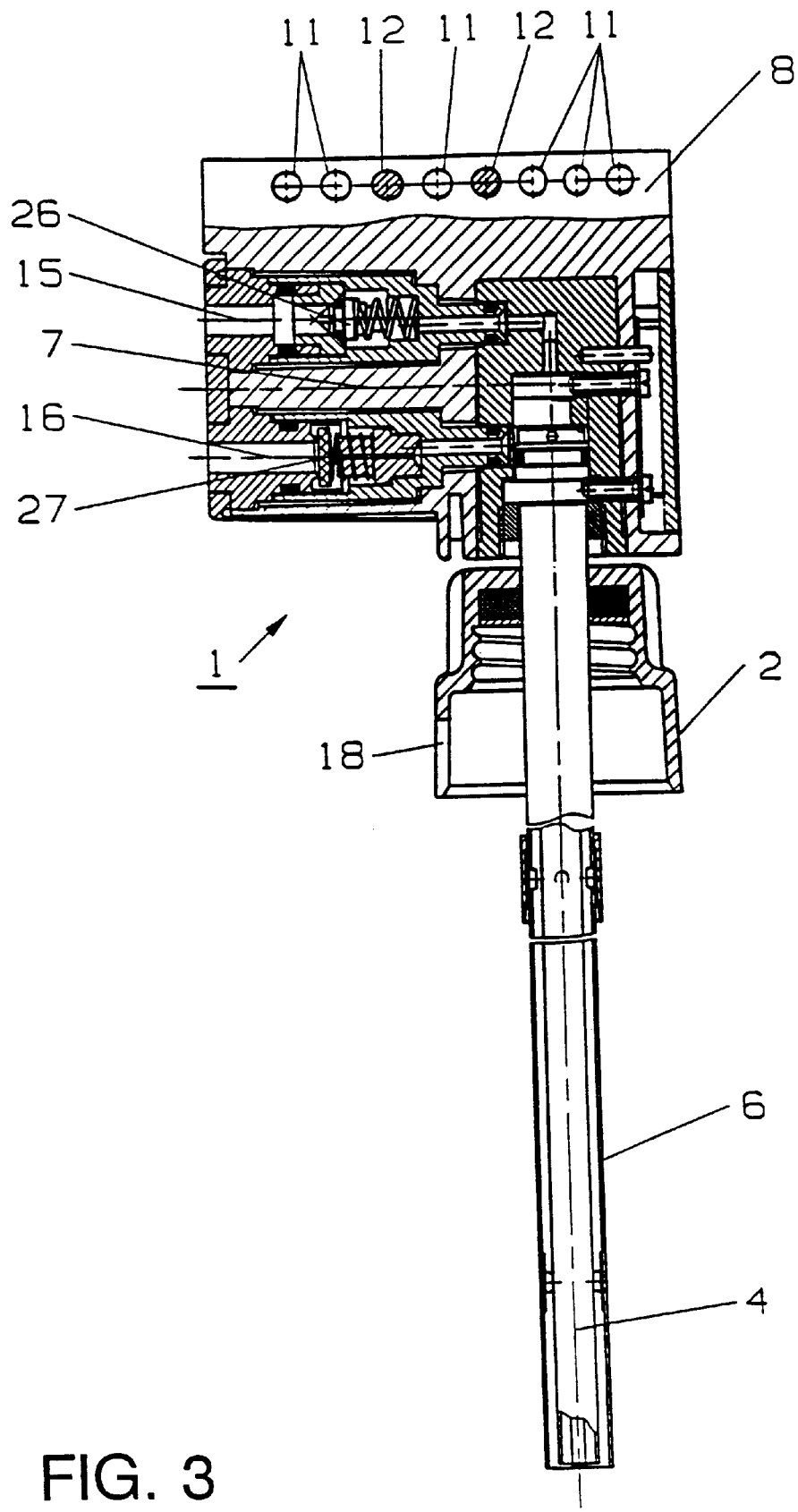
FIG. 3 is a longitudinal section of the filling adapter according to FIG. 1.
Figure 4:
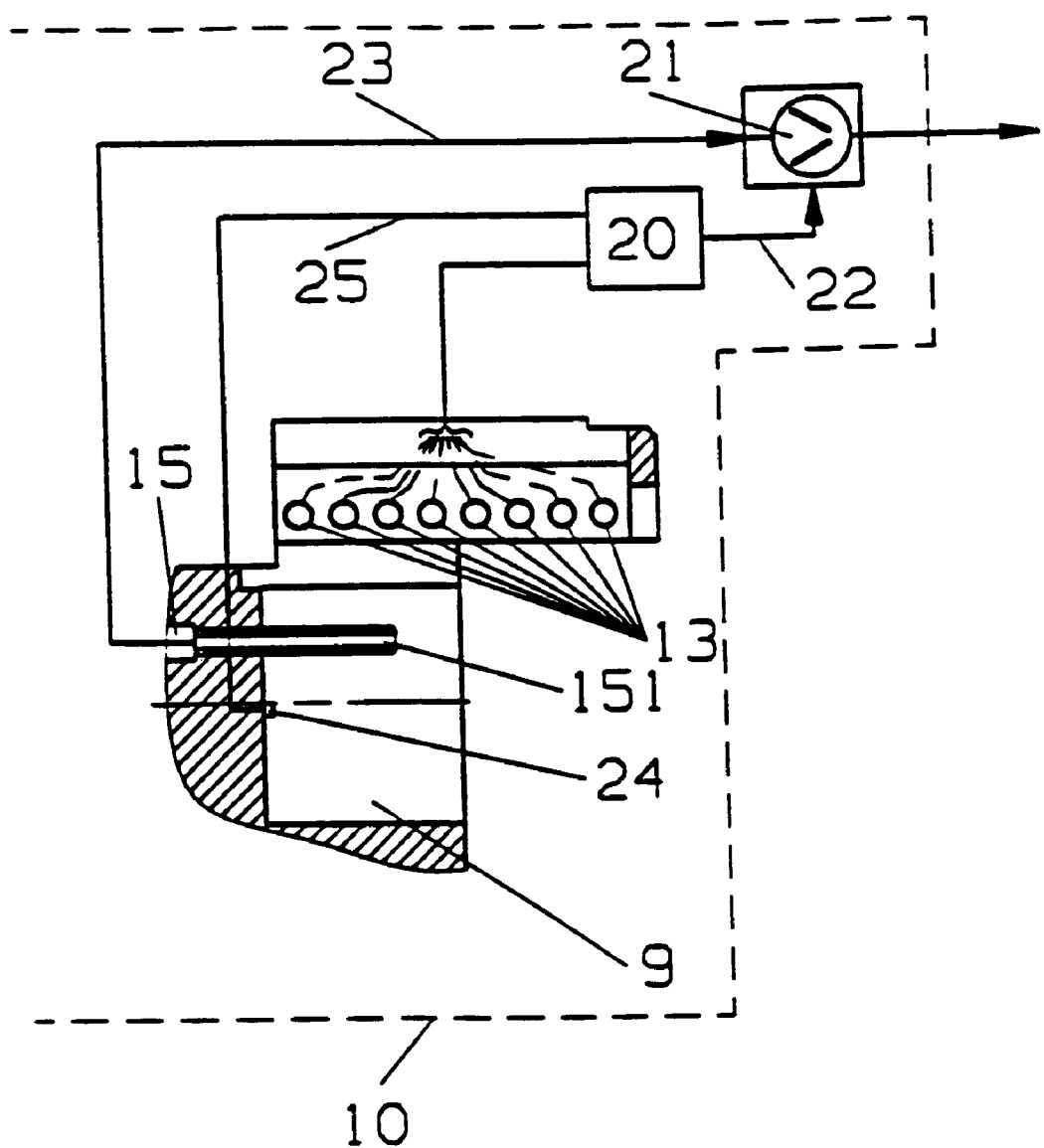

FIG. 2 shows the bottle adapter 1 with the reservoir 5 removed in the viewing direction A according to FIG. 1. Identical components are designated with the same reference numbers as in FIG. 1. FIG. 3 shows a longitudinal section through the filling adapter 1 according to FIG. 1. Identical components are designated with the same reference numbers as in FIG. 1. A nonreturn valve 26 is arranged in the filling channel 15 in the area of the coupling piece 7, and a pressure equalization valve 27 is arranged in the venting channel 16. In the position shown in FIG. 3, the nonreturn valve 26 and the pressure equalization valve 27 are in the closed position. The pressure equalization valve 27 is dimensioned such that pressure equalization is possible via the venting channel 16 in the case of a vacuum in the reservoir 5, not shown in FIG. 3. With the coupling piece 7 inserted into the filling opening 9, the valve 26 is switched into the open position by the control pin 151.

While a specific embodiment of the invention has been shown and described in detail to illustrate the application of the principles of the invention, it will be understood that the invention may be embodied otherwise without departing from such principles.

What is claimed is:

1. A liquid filling system, comprising:
   a reservoir filled with a liquid;
   a metering device;
   a filling adapter for connecting said reservoir with said metering device, said filling adapter including a liquid-specific connection piece for connecting the filling adapter to a liquid specific connection on said reservoir and code means for supplying a code detectable by said metering device representing the liquid contained in said reservoir, said code means being provided on said filling adapter in a connection area between said filling adapter and said metering device.

2. A filling adapter in accordance with claim 1, further comprising: code detection means for detecting said code, connected to a said measuring and monitoring device, said code detection means being arranged on said metering device, said measuring and monitoring device comparing said code detected with a code pattern present in a stored set and generating a control signal in the case of agreement.

3. A filling system in accordance with claim 1, wherein said code means comprises an opto-electronically detectable, coded strip.

4. A filling system in accordance with claim 1, wherein said code means includes a permanent memory (EEPROM).

5. A filling system in accordance with claim 1, further comprising:
   one of a filling channel and a venting channel located in said connection area and provided with a pressure-limiting valve.

6. A filling system in accordance with claim 1, wherein a suction system is provided extending from said connection piece into said reservoir, said suction system is designed as a filling level indicator.

7. A filling system in accordance with claim 6, wherein said filling level indicator comprises a capacitive transducer with a suction tube and with an outer tube, said outer tube being coaxial to said suction tube and being fastened insulated from said suction tube.

8. A filling system in accordance with claim 1, wherein said filling adapter has a coupling piece, which can be inserted into an insertion opening of said metering device and is aligned standing essentially at right angles to said reservoir.

9. A filling system in accordance with claim 8, wherein said connection area between said filling adapter and said metering device is an overlapping area of said coupling piece and said insertion opening.

10. A filling system in accordance with claim 1, wherein;
    said reservoir includes a star like coding piece, and said liquid specific connection piece defines a recess for receiving said coding piece.

11. A liquid anesthetic filling system comprising:
    a reservoir holding an anesthetic liquid;
    a metering device defining an insertion opening;
    a filling adapter for connecting said reservoir with said metering device, said filling adapter including a liquid-specific connection piece for connecting said filling adapter to a liquid specific connection on said reservoir, said filling adapter including a coupling piece insertable into said insertion opening of said metering device, said metering device having a connection area overlapping said coupling piece when said coupling piece is inserted into said insertion opening;
    code means on said coupling piece for indicating a code of the liquid in said reservoir;

code detection means on said connection area of said metering device and for detecting said code on said coupling piece;

measuring and monitoring means arranged with said metering device and connected to said code detection means, said measuring and monitoring means including a stored set of code patterns and comparing said code detected by said code detection means with said stored set of code patterns, said measuring and monitoring means generating a control signal as a result of said comparison.

12. A filling adapter in accordance with claim 11, wherein said code means comprises an opto-electronically detectable, coded strip.

13. A filling adapter in accordance with claim 11, wherein said code means is designed as a permanent memory (EEPROM).

14. A filling adapter in accordance with claim 11, further comprising: one of a filling channel and a venting channel located in said connection area and provided with a pressure-limiting valve.

15. A filling adapter in accordance with claim 11, wherein a suction system is provided extending from said connection piece into said reservoir, said suction system is designed as a filling level indicator.

16. A filling adapter in accordance with claim 15, wherein said filling level indicator comprises a capacitive transducer with a suction tube and with an outer tube, said outer tube being coaxial to said suction tube and being fastened insulated from said suction tube.

17. A filling system in accordance with claim 11, wherein;
said metering device includes a metering pump for removing the liquid from said reservoir, said measuring and monitoring means adjusts said metering pump according to characteristics of the fluid as represented by said code detected by said detection means.

18. A filling system in accordance with claim 11, wherein;
said reservoir includes a star like coding piece, and said liquid specific connection piece defines a recess for receiving said coding piece.

* * * * *